United States Patent [19]  [11] 4,164,561
Hautmann  [45] Aug. 14, 1979

[54] INSECT REPELLENT

[76] Inventor: Horst Hautmann, Johann-Strasse-Strasse 9, D-8858 Neuburg, Fed. Rep. of Germany

[21] Appl. No.: 791,110

[22] Filed: Apr. 26, 1977

[30] Foreign Application Priority Data

Apr. 29, 1976 [DE] Fed. Rep. of Germany ....... 2618975

[51] Int. Cl.$^2$ .......................... A01N 9/02; A01N 9/08; A01N 9/24; A01N 9/20
[52] U.S. Cl. ......................................... 424/29; 424/40; 424/46; 424/47; 424/76; 424/195; 424/324; 424/333; 424/DIG. 10
[58] Field of Search ............... 424/DIG. 10, 324, 333, 424/40, 46, 47, 29, 76

[56] References Cited

U.S. PATENT DOCUMENTS

2,323,804  7/1943  Driscoll ................................ 424/40
2,408,389  10/1946  Gertler ................................ 424/324

FOREIGN PATENT DOCUMENTS

2534765  2/1976  Fed. Rep. of Germany ............. 424/33

OTHER PUBLICATIONS

King, "Chemicals Evaluated as Insecticides & Repellents...", U.S.D.A. Handbook No. 69 Issued (May 1954), pp. 13-21, 120, 245-247 & 327.
J. of Economic Entomology, vol. 25, Oct. 1932, pp. 950-955.

*Primary Examiner*—Donald B. Moyer
*Attorney, Agent, or Firm*—Pollock, Vande Sande & Priddy

[57]  ABSTRACT

An insect repellent containing perfume which includes citral, citronella oil, and diethyltoluamide.

8 Claims, No Drawings

INSECT REPELLENT

BACKGROUND OF THE INVENTION

The present invention relates to an insect repellent. Chemical compounds which are intended to keep insects away or to drive them away have been known for a long time. These insect repellents are described in detail, for example, in the technical book entitled "Die Insektizide" (Insecticides) by Werner Perkov, pages 533–540. Among others, the following compounds are described in particular detail: phthalic acid dimethylester, 2-ethyl-hexane-1,3-diol, butopyronoxyl, dimethylcarbate, 2,3,4,5-bis-(butylene)-tetrahydrofurfurol, pyridin-2,5-dicarbonic acid-di-n-propylester, and m-toluol acid-N,N-diethylamide (diethyltoluamide). The known repellents are intended for personal use, that is to say, they must be applied upon a person's skin and thus prevent the person treated in this fashion from being stung by, for example, gnats.

Further details as to the way in which the repellent effect takes place are not known. The deterrent effect has nothing to do with an odor or taste which can be defined as being pleasant or unpleasant or otherwise as far as human sensation is concerned. It is further quite difficult to predict from the chemical identify of a composition whether such will be effective as an insect repellent.

It is known that certain insecticides also act as repellents. For example, pyrethrum spirals are set on fire and glow slowly. The developing pyrethrum vapors have a repellent effect on insects.

The German patent application laid open for inspection No. 2,534,765 also describes the repellent effect of citral, an aldehyde, which is found in volatile oils of lemons, lemon grass, and oranges.

The American market furthermore offers a product developed especially for garbage cans which is based on dichlordimethylvinylphosphate (DDVP). This product however is intended to kill insects in the garbage can; this product does not create a repellent effect.

The known repellents have only a very low vapor pressure, and therefore, do not appear to be very suitable for use as repellents in an independent vaporization mechanism. They have an effect only if they are applied to the skin because they drive insects away when these insects approach the human body. In general, it has been observed that the insects very briefly sit down on the treated skin, but then fly off again right away without, for example, stinging.

Insecticidal products based on DDVP referred to hereinabove suffer from the disadvantage that DDVP is a strongly toxic substance. Because it is not desirable to have such poisonous substances in the kitchen and, on the other hand, because application during use naturally is such that the product can readily be reached by infants, these facts represent an extremely serious disadvantage. The previously mentioned pyrethrum spirals are impractical to handle and cannot be considered for use in trash cans.

The problem therefore is to develop an insect repellent, especially for trash cans and the like, which does not possess the above-described disadvantages and which in particular will meet the following requirements:

1. Maximum effect wherein the insects are extensively kept away from the trash can. This is to prevent breeding grounds from developing in the trash cans and having disease germs spread by the insects.
2. The bad odors developing in the trash can should be extensively neutralized or covered over.
3. The repellent must practically be nontoxic because, when used in any kitchen, no toxicologically objectionable vapors must reach foods and, on the other hand, children must not be able readily to get at the product when, for example, it is used in the trash can lid.
4. The effect of such a dispenser should last as long as possible.

Numerous series of experiments conducted over a long period of time revealed that this task can be accomplished by the composition of the present invention.

SUMMARY OF THE INVENTION

The present invention is concerned with an insect repellent which consists essentially of:

(A) about 70 to 96% by weight of perfume containing about 20 to about 40% by weight of citral;

(B) about 2 to about 15% by weight of citronella oil; and (C) about 2 to about 15% by weight of diethyltoluamide.

DESCRIPTION OF PREFERRED EMBODIMENTS

The ingredients employed in the present invention are all well known. In particular, the perfume or perfume oils can be employed in all forms and types of odor. Citral can be readily combined with perfumes which do not contain such in sufficient amounts for the present invention. The perfumes are intended to include those substances defined as perfume on page 669 of the Condensed Chemical Dictionary, 8th Edition, 1971, Van Nostrand Reinhold Company, disclosure of which is incorporated herein by reference.

As stated on said page 669, a perfume is a blend of pleasantly odorous substances (usually liquids) obtained from the essential oils of flowers, leaves, fruit, roots, or wood of a wide variety of plants, either by steam distillation or solvent extraction. Perfume materials are also derived from animal sources (musk, ambergris), from resinous extracts (terpenes and balsams); they are also made synthetically.

The preferred perfumes containing the desired amount of citral include citrus oils such as lemon, lime, and orange.

The perfume can contain citronella oil, in which case the citronella oil would be present both in the perfume and as the component (B) referred to hereinabove. Examples of further perfumes include peppermint oil, lavender oil, bergamot oil, oil of thyme, safrol, irone, clove bud, cananaga, ylang-ylang, and sandalwood. Mixtures of perfumes can be used when desired.

The citral (3,7-dimethyl-2,6-octadienal) employed in the present invention is an easily mobile, slightly yellowish oil that smells of lemons. Citral can be found in numerous etheric oils, especially lemon grass oil and lemon oil.

Citronella oil is a colorless, yellow to yellow-brown liquid which has a strong smell of lemons or balm mint and which has a burning taste. The odor is caused primarily by citronellal; the quantitative main constituent is geraniol, plus borneol, camphene, dipentene, etc.

Diethyltoluamide has become known particularly because of its good repellent action against mosquitoes. The compound which is obtained from a reaction of m-toluyl acid chloride with diethylamine is a bright liquid with a boiling point of 111° C./mm Hg; it is insoluble in water and soluble in most organic solvents.

The insect repellent of the present invention contains the perfume in amounts between about 70 to about 96%; preferably about 80 to about 90%; and most preferably about 85.70% by weight; the citronella oil in amounts of about 2 to about 15%; preferably about 5 to about 10%; and most preferably about 7.15% by weight; and the diethyltoluamide in amounts of about 2 to about 15%; preferably about 5 to about 10%; and most preferably about 7.15% by weight. The above amounts are based upon the total amount of perfume, citronella oil, and diethyltoluamide in the insect repellent. The composition preferably consists essentially of the foregoing components, meaning that other ingredients can be employed in amounts which do not seriously impair the above-described primary function of the required constituents. The amount of citral included in the perfume is from about 20 to about 40%, preferably about 25 to about 35%, and most preferably about 30% by weight.

The insect repellents according to the present invention can be prepared by merely mixing the constituents at room temperature. A slowly running stirring mechanism is sufficient.

By means of dosing pumps, the liquid composition can be placed on a suitable carrier material. The carrier can be natural or synthetic fiber, foam, or other carrier having a structure (e.g., porosity) from which the active material can evaporate. Examples of carriers include cellulose and asbestos. Preferably the carrier is a cellulose plate. These impregnated plates are pushed or squeezed into a housing or case (e.g., made of synthetic plastic) which has enough openings so that the active substance can evaporate. The housing can then be glued into the lid of a trash can either directly or by means of a suspension device. The active substances evaporate and create an atmosphere in the trash can which will repel insects.

For practical purposes, the product can be packaged in aluminum pouches after production so that no active substance can evaporate until it is ready for use.

Other advantages and features of the invention will emerge from the following description of an example:

(a) On a laboratory scale, a mixture was made consisting of 85.7% lemon perfumes containing about 30% citral; 7.15% citronella oil, and 7.15% diethyltoluamide. Of this mixture, 3.5 g were placed on a cellulose plate with dimensions of 55×55×2.5 mm. The cellulose is solidified but relatively unprocessed cellulose having the formula $C_6H_{10}O_5$. These cellulose plates were placed in plastic housings with sufficient evaporation openings. These devices were then used for biological tests.

(b) A sample made as described under (a) was tested as follows. Two garbage cans were placed in a room with a size of 22 m³. A plastic housing containing cellulose plate prepared above was affixed in the top of one of the cans (not affixed in the lid but on the upper half of the inner side of the can). Both garbage cans were lined on the entire inside with adhesive tape (e.g., strips) and dead flies were put in. Also into each can was placed equal amounts of cut onions and cheese. The cans were kept closed for 24 hours and then they were opened. One hundred and fifty flies (musca domestica [housefly]) were let into the room. The room temperature was 24° C.±1° C. and the relative humidity was 55%±5%. After a week, the flies which had flown into the cans and had gotten stuck there were counted. Only 19 flies had flown into the trash can with the insect repellent of the present invention; whereas, 81 flies had flown into the trash can without the repellent.

(c) The insect repellent according to the invention described under (a) was once again tested under the conditions described in (b). The experiment now extended over 30 days. Assuming that the flies which in each case penetrated the trash can without repellent to be 100%, the following values were obtained:

|  | Time (days) | | | |
| --- | --- | --- | --- | --- |
|  | 1 | 8 | 16 | 30 |
| Trash can without repellent | 100% | 100% | 100% | 100% |
| Trash can with repellent according to the invention | 75% | 60% | 61% | 36% |
|  | flies that flew in, in % | | | |

As we can see from the figures, the effect increases as time goes on. It is to be assumed that the evaporating repellent is precipitated on the surface of the trash can and as a result a stronger effect is obtained.

(d) The following samples were made in the laboratory:

I. Cellulose plate 55×55×2.5 mm. impregnated with 3.5 g diethyltoluamide.

II. Cellulose plate 55×55×2.5 mm, impregnated with 3.5 g of citrus perfume with 30% citral.

III. Cellulose plate 55×55×2.5 mm, impregnated with 3.5 g of the insect repellent according to the present invention.

Four trash cans with a volume of about 15 liters were coated on the inside with a glue. Into each can were placed about 5 g cheese, 10 g onions, and one dead fly as decoy. The above-described samples were affixed in the top of three trash cans respectively and the four trash cans were kept closed for 24 hours. After that time they were set up in a room with a size of 25 m³ and were opened. Next, 2,000 houseflies (musca domestica) were released in the room. After 30 minutes, 1 hour, 2 hours, 4 hours, 5 hours, and 24 hours, the flies which had become stuck were counted in the individual cans. The results are shown in the following table:

|  | Number of flies stuck in can | | | | | |
| --- | --- | --- | --- | --- | --- | --- |
|  | 30 min. | 1 hr. | 2 hrs. | 4 hrs. | 5 hrs. | 24 hrs. |
| Blind experiment | 8 | 37 | 90 | 150 | 170 | 200 |
| I | 3 | 8 | 20 | 40 | 44 | 55 |
| II | 1 | 14 | 37 | 100 | 110 | 130 |
| III | 2 | 2 | 13 | 15 | 17 | 27 |

It is readily apparent that in the formulation according to the present invention a combined effect which was not to be expected after the individual results is achieved.

The invention reveals the following advantages; in particular, the use of the product according to the invention:

(a) keeps insects away, enables trash cans to be kept hygienically maintained and no disease germs are carried away;

(b) the unpleasant trash can odor is masked;

(c) as a result of the etheric oils in the perfume oil, there is mild disinfection.

Compared to the products so far placed on the market, the substance according to the present invention is distinguished by the fact that it contains no toxicological constituents whatsoever.

Another special advantage of the present invention is the long-lasting and sustained effect of the product. In laboratory experiments it was possible to prove that the product has a repellent effect even after being used for three months.

The insect repellent according to the present invention can be used in household garbage cans, large trash cans, and other waste containers. It is also possible to attach the product in storage rooms, etc., in which foodstuffs are kept. One main area of utilization is the trash can (waste basket), for example in the kitchen.

What is claimed is:

1. A housefly repellent which consists essentially of:
   (A) about 85.70% by weight of perfume which contains 30% by weight of citral;
   (B) about 7.15% by weight of citronella oil; and
   (C) about 7.15% by weight of diethyltoluamide.

2. The housefly repellent of claim 1 wherein said perfume is lemon, lime, or orange.

3. A porous carrier impregnated with the housefly repellent of claim 1.

4. The housefly repellent of claim 1 wherein said diethyltoluamide is m-diethyltoluamide.

5. The housefly repellent of claim 1 wherein said perfume is lemon.

6. The housefly repellent of claim 1 which consists essentially of:
   (A) about 85.70% by weight of a lemon perfume containing about 30% by weight of citral;
   (B) about 7.15% by weight of citronella oil; and
   (C) about 7.15% by weight of m-diethyltoluamide.

7. A cellulose porous carrier impregnated with the housefly repellent of claim 1.

8. An asbestos porous carrier impregnated with the housefly repellent of claim 1.

* * * * *